United States Patent [19]

Osterburg et al.

[11] Patent Number: 4,709,106

[45] Date of Patent: Nov. 24, 1987

[54] PROCESS FOR DEODORIZING ISOPROPYL ALCOHOL

[75] Inventors: Günther Osterburg, Rheurdt; Karl-Heinz Gluzek, Alpen; Wilhelm Neier, Rheinberg, all of Fed. Rep. of Germany

[73] Assignee: Deutsche Texaco Aktiengesellschaft, Hamburg, Fed. Rep. of Germany

[21] Appl. No.: 1,131

[22] Filed: Jan. 5, 1987

[30] Foreign Application Priority Data

Mar. 12, 1986 [DE] Fed. Rep. of Germany ....... 3608202

[51] Int. Cl.$^4$ ...................... C07C 29/76; C07C 31/10
[52] U.S. Cl. ..................................... 568/917; 568/922
[53] Field of Search ................................. 568/917, 922

[56] References Cited

U.S. PATENT DOCUMENTS

| | | | |
|---|---|---|---|
| 2,628,986 | 2/1953 | Wallace et al. | 568/917 |
| 2,792,344 | 5/1957 | Tidwell | 568/917 |
| 3,373,180 | 3/1968 | Glass et al. | 568/917 |
| 3,433,841 | 3/1969 | Dehn et al. | 568/917 |
| 4,219,685 | 8/1980 | Savini | 568/917 |

*Primary Examiner*—J. E. Evans
*Attorney, Agent, or Firm*—Robert A. Kulason; James J. O'Loughlin; Robert B. Burns

[57] ABSTRACT

A process for deodorizing technical-grade isopropyl alcohol by contacting the alcohol with a strongly acidic cation exchange resin loaded with palladium in ionic form is provided.

10 Claims, No Drawings

PROCESS FOR DEODORIZING ISOPROPYL ALCOHOL

FIELD OF THE INVENTION

This invention relates to a process for deodorizing isopropyl alcohol. More particularly, it relates to the deodorizing of isopropyl alcohol which has been produced by the catalytic hydration of propene in the presence of a sulfonated styrene-divinylbenzene resin catalyst.

Isopropyl alcohol is produced by the reaction of propene with sulfuric acid or by direct hydration on a sulfonated cation exchange resin. This isopropyl alcohol contains traces of different compounds which impart to the technical-grade product an unpleasant odor that makes it unsuitable for a variety of uses and, particularly, for use in the cosmetic and pharmaceutical industry.

The contaminants considered responsible for causing the odor in isopropyl alcohol are only partly detectable by gas chromatographic analyses. Their content in the technical-grade alcohol is in the order of parts per billion (ppb). They are comprised of organic sulfur compounds, such as hydrogen sulfide, carbonyl sulfide, and mercaptans. At the present time, expensive treatment procedures have been necessary, such as distillation and adsorption processes, to free the technical-grade alcohol from these substances. Deodorization by active carbon treatment has been performed for many years. However, it is necessary to reactivate the active carbon at regular intervals by expensive steam treatment. Even this treatment has limitations. Only a few active carbon absorbents are suitable. Some produce too many by-products, such as acetone, or cannot be reactivated, or can be reactivated only to a limited extent or are not sufficiently efficient for deodorization.

DISCLOSURE STATEMENT

U.S. Pat. No. 2,857,436 discloses a process for improving the odor of lower technical-grade alcohols by contacting them with a fine silicious iron material having a large surface area. In another embodiment of the process of said patent specification, the lower alcohols are contacted with unglazed porcelain and steel wool in order to improve the odor.

U.S. Pat. No. 2,729,682 discloses a process for improving the odor of isopropyl alcohol by adding during the production $C_4$–$C_6$ mono-olefins to the propylene stream, reacting with sulfuric acid, and hydrolyzing the reaction product while simultaneously reacting at temperatures of up to 300° C. the $C_4$–$C_6$ olefin contained therein together with the contaminants causing the odor to form higher boiling contaminants. The purified isopropyl alcohol is then obtained by extractive distillation with water.

U.S. Pat. No. 4,219,685 disclosed the deodorization of $C_2$ and $C_3$ alcohols at an elevated temperature in the presence of hydrogenation-active metals, particularly nickel and platinum metals, supported on inorganic material.

U.S. Pat. No. 4,340,769 discloses a method for the preparation of lower aliphatic alcohols by the hydration of an olefin over a catalyst. This disclosure is incorporated by reference.

The processes of the prior art are either complicated and expensive, or during the treatment suggested produce additional contaminants, particularly ketones and ethers.

It is the object of this invention to make available a deodorization process that largely takes away the unpleasant odor of the technical-grade product, that is easy to handle and involves low cost, and that for its part does not form objectionable by-products, such as ketones and ethers.

SUMMARY OF THE INVENTION

In accordance with the invention, isopropyl alcohol which is malodorous or contains an objectionable odor for certain uses is deodorized by contacting the isopropyl alcohol with a strongly acidic cation exchange resin catalyst which has been treated with palladium in ionic form and which has been neutralized with a mixture of an alkali metal or an alkaline earth metal hydroxide and halide.

DETAILED DESCRIPTION OF THE INVENTION

It has been discovered that isopropyl alcohol having an objectionable odor for many commercial applications may be efficiently and economically deodorized by contacting the isopropyl alcohol with a strongly acidic ion exchange resin catalyst which has been treated with or impregnated with palladium in an ionic form, as with a palladium salt and which has been neutralized with a mixture of an alkaline earth metal hydroxide or an alkali metal hydroxide and halide.

The isopropyl alcohol requiring a purification treatment may contain sulfur compounds in concentrations measured in parts per billion. In general, the malodorous sulfur compounds may be present in a concentration ranging from about 0.1 to 50 parts per billion. More common concentrations of malodorous components is from about 1 to 25 parts per billion.

The catalyst employed in this process is a palladium-treated or impregnated, neutralized strongly acidic ion exchange resin catalyst. A preferred synthetic resin catalyst is a sulfonated styrene-divinyl benzene resin catalyst. Specific preferred synthetic resin catalysts are Amberlyst 15 from Rohm & Haas and LEWATIT SPC 118 from Bayer AG.

The catalyst employed in the process of this invention is produced by (a) loading a strongly acidic cation exchange resin with palladium in ionic form, neutralizing with a quantity of a mixture of alkali—or alkaline earth hydroxide with halide of 95:5 to 75:25, the alkali or alkaline earth ions being made available at most at the equivalent amount relative to the yet free sulfonic acid groups of the cation exchange resin, or by (b) loading a strongly acidic cation exchange resin completely neutralized with alkali—or alkaline earth hydroxide with palladium in ionic form, subjecting it to aftertreatment with halogen hydracid while adjusting the acid concentration surrounding the resin at 0.01 n to 0.5 n, and thereafter contacting it with the alcohol to be deodorized.

It was surprisingly found that a strongly acidic cation exchange resin loaded with palladium in ionic from and subjected to neutralizing treatment is effective for deodorizing isopropyl alcohol produced by catalytic hydration of propene. The deodorization according to the invention is performed by passing the alcohol over the fixed-bed deodorizing resin at atmospheric pressure and ambient temperature. Higher pressures can be employed, but are not necessary.

Elevated temperatures should be avoided, even if the deodorizing resin is present in practically completely neutralized form. The deodorization is generally performed at 0° to 50° C., particularly at 10° to 30° C., and preferably at 15° to 25° C.

Since the deodorization proceeds very rapidly, high charges of the fixed-bed deodorizing resin, for instance from 0.1 to 15 l of alcohol/liter of cation exchange resin.h are possible. Preferably 0.4 to 10 l of alcohol/liter of cation exchange resin.h can be put through.

The palladium concentration or load should range from about 0.1 to 25 g (calculated as metal) per liter of cation exchange resin, a preferred range is from 0.1 to 10 g of palladium with the most preferred concentration being from about 5 to 8 (calculated as metal) per liter of cation exchange resin.

Complete loading of the strongly acidic cation exchange resin is aimed at in order to largely avoid acidic catalyst spots. These result in side reactions, particularly the formation of ether and further condensation of acetone that has formed, which is undesired.

According to a preferred embodiment of the process of the invention according to variant (a), the palladium-loaded, strongly acidic cation exchange resin is neutralized with a mixture of alkali—or alkaline earth hydroxide and -halide at a hydroxide/halide ratio of 85:15 to 90:10. Particularly a mixture of NaOH/NaCl is used.

According to a preferred embodiment of the process of the invention according to variant (b), the aftertreatment with halogen hydracid is performed with the acid concentration being adjusted at 0.01 to 0.1 n. Hydrochloric acid is preferred for the aftertreatment.

The process according to the invention is particularly economically performed by using isopropyl alcohol that has previously been subjected to predeodorization on a strongly acidic cation exchange resin loaded with silver ions.

The strongly acidic cation exchangers used as support resins are those based on synthetic resin, particularly styrene/divinyl benzene mixed polymerizates with sulfonic acid groups on the aromatic core which are also used for producing the isopropyl alcohol from propene by direct hydration. Preferred resins are those of the type Amberlyst TM 15 from Rohm & Haas Co., U.S.A., or LEWATIT TM SPC 118 from Bayer AG, Leverkusen.

The used deodorizing resin can be regenerated, the metal being recovered.

For evaluating the odor a sample is diluted with inodorous water in a ground glass cylinder similar to a test tube with glass stopper, thoroughly mixed, and the odor is evaluated. The alcohol is classified by having the odor graded accordingly by several persons:

| Quality | Grading | | |
|---------|---------|---|---|
| IPA SS = | 1.0-1.4 | ↓ | deterioration |
| IPA S = | 1.5-2.4 | ↓ | in |
| IPA = | 2.5-3.4 | ↓ | quality |
| IPA K = | 3.5-4.0 | ↓ | |

The final grade results from the sum of points divided by the number of testers.

The process according to the invention is suitable both for deodorizing the dry isopropyl alcohol and for deodorizing mixtures of the alcohol with water, and particularly azeotropic isopropyl alcohol.

The following examples illustrate the invention.

EXAMPLE 1 (COMPARISON EXAMPLE)

Palladium in metallic form supported on inorganic material is capable of completely eliminating the sulfur-containing odorants contained in technical-grade isopropyl alcohol. The catalytic activity of the metallic palladium resulted in an intolerably high conversion of isopropyl alcohol (IPA) into acetone or to a correspondingly high contamination of IPA and, thus, is unsuitable for deodorizing IPA.

TABLE I

|  | 1.1 | 1.2 | 1.3 | 1.4 |
|---|---|---|---|---|
| Palladium, wt. % | 5 | 0.5 | 0.5 | 0.5 |
| Valence of the metal | 0 | 0 | 0 | 0 |
| Support material | $Al_2O_3$ | $Al_2O_3$ | $Al_2O_3$ | $Al_2O_3$ |
| Temperature, °C. | 20 | 20 | 20 | 50 |
| Load, 1/V | 0.35 | 0.35 | 1.75 | 1.75 |
| Duration, days | 60 | 1 | 1 | 1 |
| Odor | 1 n | 1 | 1 | 1 |
| U.V. curve | Ketone | Ketone | Ketone | Ketone |
| Ketone, ppm | 300 | 300 | 300 | 580 | n = new foreign odor

After treatment of IPA the catalyst 1.2 through 1.4 tended to autoignition.

Palladium in ionic form supported on a strongly acidic cation exchanger also showed good elimination of sulfur-containing odorants from IPA as the metallic form of palladium. This case also resulted in an unsatisfactory catalytic conversion of IPA. The combination of catalytically active palladium and the catalytically acting acid groups of the cation exchanger resulted in intolerable contamination of IPA by different by-products.

EXAMPLE 2

A strongly acidic cation exchanger loaded with palladium ions, 7.6 g of Pd/l of Lewatit TM SPC 118 from Bayer AG, was contacted with isopropyl alcohol at room temperature for an extended period. The odorants previously present were eliminated, but considerable new additional odors, diisopropyl ether and acetone were formed leading to deterioration of the IPA quality detectable by U.V. spectroscopy.

When first neutralizing the same palladium-loaded cation exchanger with NaOH, prior to treatment of IPA, no further analytical changes were detectable, with the exception of acetone formation, see table II.

EXAMPLE 3

Over a column of 150 ml of a strongly acidic cation exchanger, Lewatit TM SPC 118, loaded with 0.5 g of Pd/l, 300 ml of isopropyl alcohol at 50° C. were passed per hour. An alcohol sample taken after two hours of operating time was evaluated as follows:

Odor: The odorants contained in the technical-grade IPA had been completely eliminated. A new stuffy smell was perceptible.

Permanganate time: The permanganate time of the IPA had deteriorated from 35 minutes to 10 minutes (ASTM D 1363).

By gaschromatographic analysis 60 ppm of diisopropyl ether and 120 ppm of acetone were detected.

The U.V. spectroscopic examination showed a deterioration as compared to the IPA feed.

When performing the same experiment with the same deodorizing resin, but which had been neutralized with NaOH, no further qualitative deterioration of the IPA, was noticed except for too high a formation of acetone of 200 ppm. The odorants previously contained had been completely eliminated.

TABLE II

Catalytic Side Effects When Using Palladium-Loaded Cation Exchangers
(Life Time Test)

| Cation Exchanger (anhydrous) | SPC 118[1] | SPC 118[2] |
|---|---|---|
| Pd Load g/l | 7.6 | 7.6 |
| $SO_3^{(-)}$ | $H^+$ | $Na^+$ |
| Resin quantity ml | 40 | 40 |
| IPA quantity ml | 60 | 60 |
| Life time days | 8 | 8 |
| Temperature °C. | 20 | 20 |
| Evaluation: GC Analysis | | |
| Lower Hydrocarbons ppm | less than 10 | less than 10 |
| IPE ppm | 30 | less than 10 |
| Acetone ppm | 120 | 2,600 |

U.V. absorption:
[1] In the range of 220-260 mµ elevated extinction resulting from unknown U.V.-active byproducts were detected.
[2] In this case only the known extinction maximum of 272 mµ for acetone was found.

EXAMPLE 4

During the production of neutralized palladium-loaded strongly acidic cation exchanger for the deodorization of IPA, the catalytic activity of the palladium increased as the amount of neutralizing agent increased.

(a) 100 ml of a strongly acidic cation exchanger, Amberlyst TM 15, loaded with 5 g of palladium/1 of resin, the free equivalent of acid groups of which had been neutralized at 100% during one hour by addition of 1 n NaOH down to a pH value of 9.0 in the eluate were used for deodorizing isopropyl alcohol. To this end 300 ml of IPA/h were passed over the deodorizing resin from the top to the bottom of a column during 7 days at 20° C. The odorants were completely eliminated. The acetone content was constantly 300 ppm.

(b) 100 ml of the above described resin the free equivalent of acid groups of which had been neutralized for 85% during one hour by addition of 1 n NaOH down to a pH value of 3.0 in the eluate, were used for deodorizing IPA. 300 ml of IPA/h were passed from the top to the bottom of a column during 7 days at 20° C. The odorants were completely eliminated. The acetone content was constantly 60 ppm.

EXAMPLE 5

During the production of neutralized, palladium-loaded strongly acidic cation exchange resins for the deodorization of IPA activation of the catalytically active palladium can be largely avoided when limiting the degree of neutralization to 85% of the free sulfonic acid equivalent and adding chloride ions to the neutralizing agent.

For comparison a strongly acidic cation exchanger, Amberlyst TM 15, loaded with 5.75 g of Pd/1 resin was produced and treated in several equal portions with the neutralizing agents listed in Table III. Subsequently, 100 ml of each resin portion were used for deodorizing IPA. During 48 hours 300 ml of IPA/h were passed through at 20° C. In each experiment the deodorization was good. The formation of acetone is shown in the following table:

TABLE III

| Neutralizing Agent | Neutralization Equivalent | Acetone ppm |
|---|---|---|
| 1 n NaOH | 85% | 61 |
| 1 n NaOH/NaCl 85:15 | 85% | 5 |
| 1 n NaOH/NaCl 90:10 | 85% | 5 |
| 1 n NaOH/NaCl 95:5 | 85% | 13 |
| 1 n NaOH/NaCl 85:15 | 100% | 50 |

EXAMPLE 6

Neutral, palladium-loaded strongly acidic cation exchangers for the deodorization of IPA can also be produced by loading preneutralized or neutral types of commercial cation exchangers.

In this case, too, catalytic activation of palladium cannot be precluded. By aftertreatment with dilute hydrochloric acid (0.1 n) down to a pH value of 2 in the eluate the catalytically active palladium is repulsed as hexachloropalladinate and the desired catalytic inactivity of the deodorizing resin is attained. After this treatment 85-90% of the mentioned sulfonic acid equivalent are present in the bound neutral form.

600 l of a neutralized strongly acidic cation exchanger of the type Amberlyst TM 15 loaded with 5 g of Pd/1 of resin and produced in this way were used for deodorizing IPA. During 142 days 10,224 m³ of IPA were passed through the resin bed from the top to the bottom at a load of 3 m³ of IPA/h and an average temperature of 20° C. The odorants contained in the technical-grade IPA were completely eliminated. No formation of acetone was observed.

EXAMPLE 7

In two towers having a diameter of 0.2 m and a height of 1.0 m and connected in series 30 l of a neutral strongly acidic cation exchanger of the type Lewatit TM SPC 118 loaded with 8 g of silver/1 of resin were used in the first tower and 30 l of a strongly acidic cation exchanger of the type Amberlyst TM 15 loaded with 7.6 g of Pd/1 of resin, the free equivalent of acid groups had been neutralized at 90% were placed in the second tower.

Isopropyl alcohol produced by catalytic hydration of propene, purified and dried by distillation, but having an intolerable odor was passed over the two towers at a throughput of 200 lh.

This throughput corresponds in each tower to a load of 6.6 l/l of resin. Both after the first tower with silver-loaded resin and after the second tower with palladium-loaded resin no analytically detectable changes in the IPA could be traced. The olfactory evaluation up to an operating time of 56 days showed that most of the odorants contained in the IPA feed were eliminated after the first tower (odor grading 1.5–2.0) and that all of them were eliminated after the second tower (odor grading 1.0).

Even after 56 days the two deodorizing resins did not show any decrease in deodorizing efficiency.

The foregoing examples illustrate the surprising effectiveness of the process of the invention for deodorizing and substantially upgrading isopropyl alcohol.

What is claimed is:
1. A process for deodorizing isopropyl alcohol characterized by containing trace amounts of odor-forming components which comprises contacting said isopropyl alcohol with a strongly acidic cation exchange resin catalyst wherein said catalyst has been treated by the steps comprising
(a) loading a strongly acidic cation exchange resin with palladium in ionic form, neutralizing it with a quantity of a mixture of alkali—or alkaline earth hydroxide and -halide at a hydroxide/halide ratio of 95:5 to 75:25, the alkali or alkaline earth ions being made available at the equivalent amount relative to the free sulfonic acid groups of the cation exchange resin, or
(b) loading a strongly acidic cation exchange resin completely neutralized with alkali—or alkaline earth hydroxide with palladium in ionic form, subjecting it to aftertreatment with halogen hydracid, while adjusting the acid concentration surrounding the resin at 0.01 n to 0.5 n.

2. Process according to claim 1 which comprises neutralizing the palladium-loaded strongly acidic cation exchange resin with a mixture of alkali—or alkaline earth hydroxide and -halide at a hydroxide/halide ratio of 85:15 to 90:10.

3. Process according to claim 1 wherein a mixture of NaOH/NaCL is employed.

4. Process according to claim 1 in which said aftertreatment with halogen hydracid is conducted at an acid concentration ranging from 0.01 to 0.1 n.

5. A process according to claim 1 in which said aftertreatment is conducted with hydrochloric acid.

6. A process according to claim 1 in which said palladium ions are employed in an amount ranging from 0.1 to 10 g (calculated as metal) per liter of resin.

7. A process according to claim 6 in which said palladium ions are employed in an amount ranging from 5 to 8 g (calculated as metal) per liter of resin.

8. Process according to claim 1 in which the treatment rate ranges from about 0.4 to 10 l of alcohol/liter of resin.h.

9. Process according to claim 1 in which said deodorization is conducted at 10° to 30° C.

10. Process according to claim 1 in which said isopropyl alcohol is first subjected to predeodorization on a silver ions-loaded strongly acidic cation exchange resin.

* * * * *